(12) United States Patent
Brunnarius

(10) Patent No.: US 8,388,620 B2
(45) Date of Patent: Mar. 5, 2013

(54) IMPLANT LOCKING DEVICE AND CORRESPONDING IMPLANT

(75) Inventor: Yann Brunnarius, Chatuzange le Goubet (FR)

(73) Assignee: Tornier SAS, Saint-Ismier (FR)

( * ) Notice: Subject to any disclaimer, the term of this patent is extended or adjusted under 35 U.S.C. 154(b) by 82 days.

(21) Appl. No.: 12/991,427

(22) PCT Filed: May 7, 2009

(86) PCT No.: PCT/EP2009/055540
§ 371 (c)(1),
(2), (4) Date: Jan. 28, 2011

(87) PCT Pub. No.: WO2009/135901
PCT Pub. Date: Nov. 12, 2009

(65) Prior Publication Data
US 2011/0295254 A1    Dec. 1, 2011

(30) Foreign Application Priority Data
May 7, 2008  (FR) ...................................... 08 53040

(51) Int. Cl.
*A61B 17/56* (2006.01)
(52) U.S. Cl. ........................................................ 606/64
(58) Field of Classification Search .............. 606/62–68, 606/79, 80, 84, 85, 60
See application file for complete search history.

(56) References Cited

U.S. PATENT DOCUMENTS

| 4,237,875 | A | 12/1980 | Temanini | |
|---|---|---|---|---|
| 5,578,035 | A | 11/1996 | Lin | |
| 6,287,310 | B1 * | 9/2001 | Fox | 606/63 |
| 6,355,069 | B1 * | 3/2002 | DeCarlo et al. | 623/23.26 |
| 6,887,271 | B2 * | 5/2005 | Justin et al. | 623/13.14 |
| 7,074,224 | B2 * | 7/2006 | Daniels et al. | 606/80 |
| 7,763,021 | B2 * | 7/2010 | Cole et al. | 606/64 |

FOREIGN PATENT DOCUMENTS

| DE | 4447057 A1 | 4/1996 |
|---|---|---|
| FR | 2104108 A | 4/1972 |

OTHER PUBLICATIONS

International Search Report, PCT/EP2009/055540, Oct. 6, 2009.

* cited by examiner

*Primary Examiner* — Pedro Philogene
(74) *Attorney, Agent, or Firm* — Faegre Baker Daniels LLP

(57) ABSTRACT

This insertion and locking device (1) for an implant in a long bone comprises an elongate body (2) designed to be received in a medullary canal of the long bone, the body defining, in a first position called the insertion position, a first transverse size and, in a second position called the locking position, a second transverse size greater than the first transverse size. This device furthermore comprises drive mechanism (8) suited to enable the body (2) to move from the first position to the second position. In addition, the elongate body (2) comprises a central member (3) defining a main axis and at least one locking member (6) defining at least one axis of movement distinct from the main axis, the or each locking member (6) being suited to anchoring itself in the long bone under the effect of the drive mechanism.

22 Claims, 6 Drawing Sheets

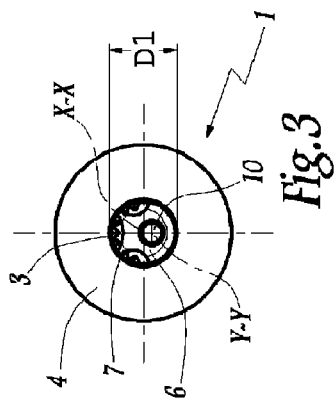
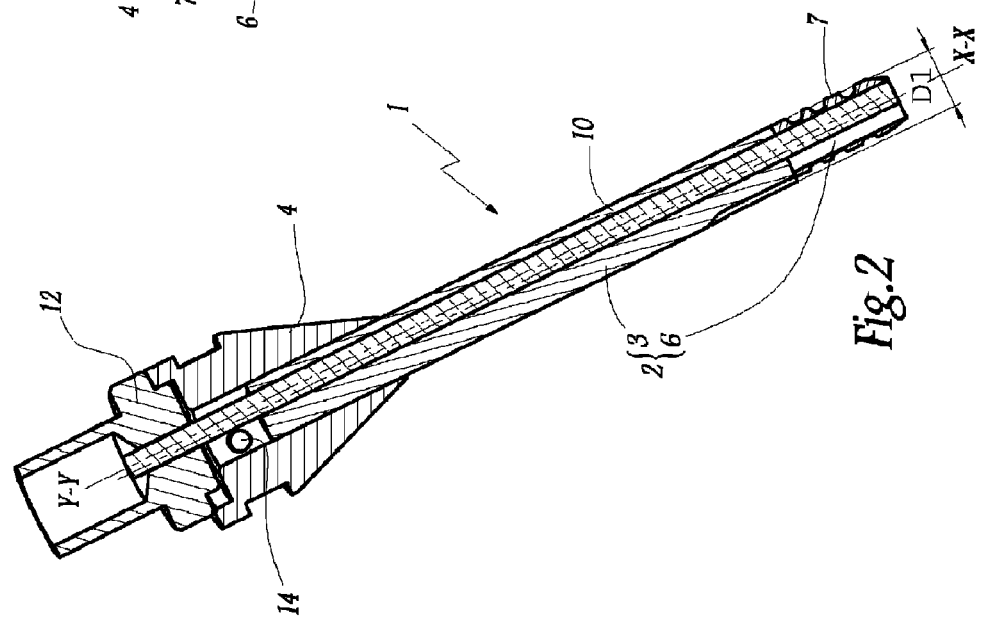
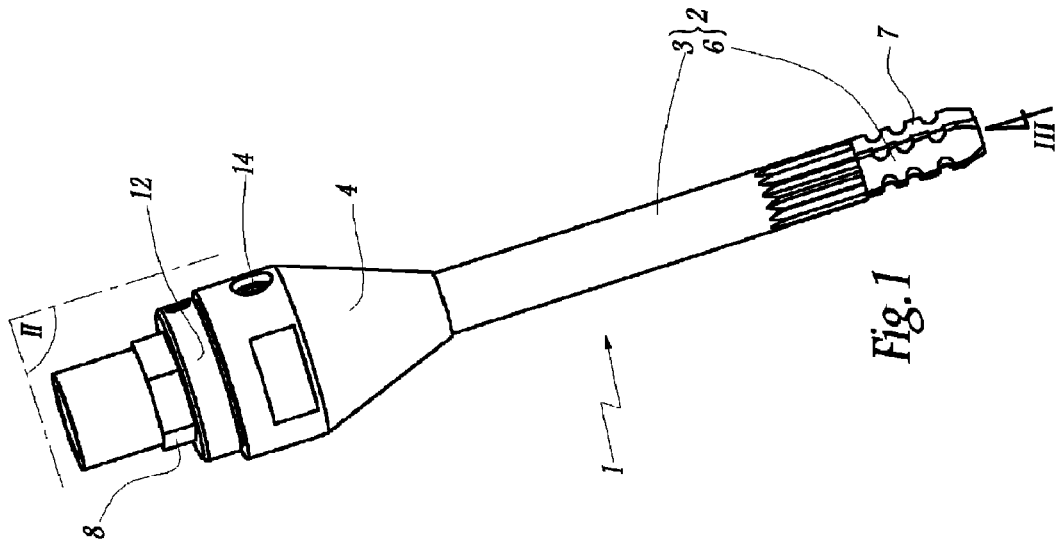

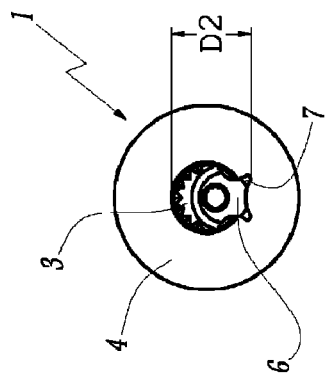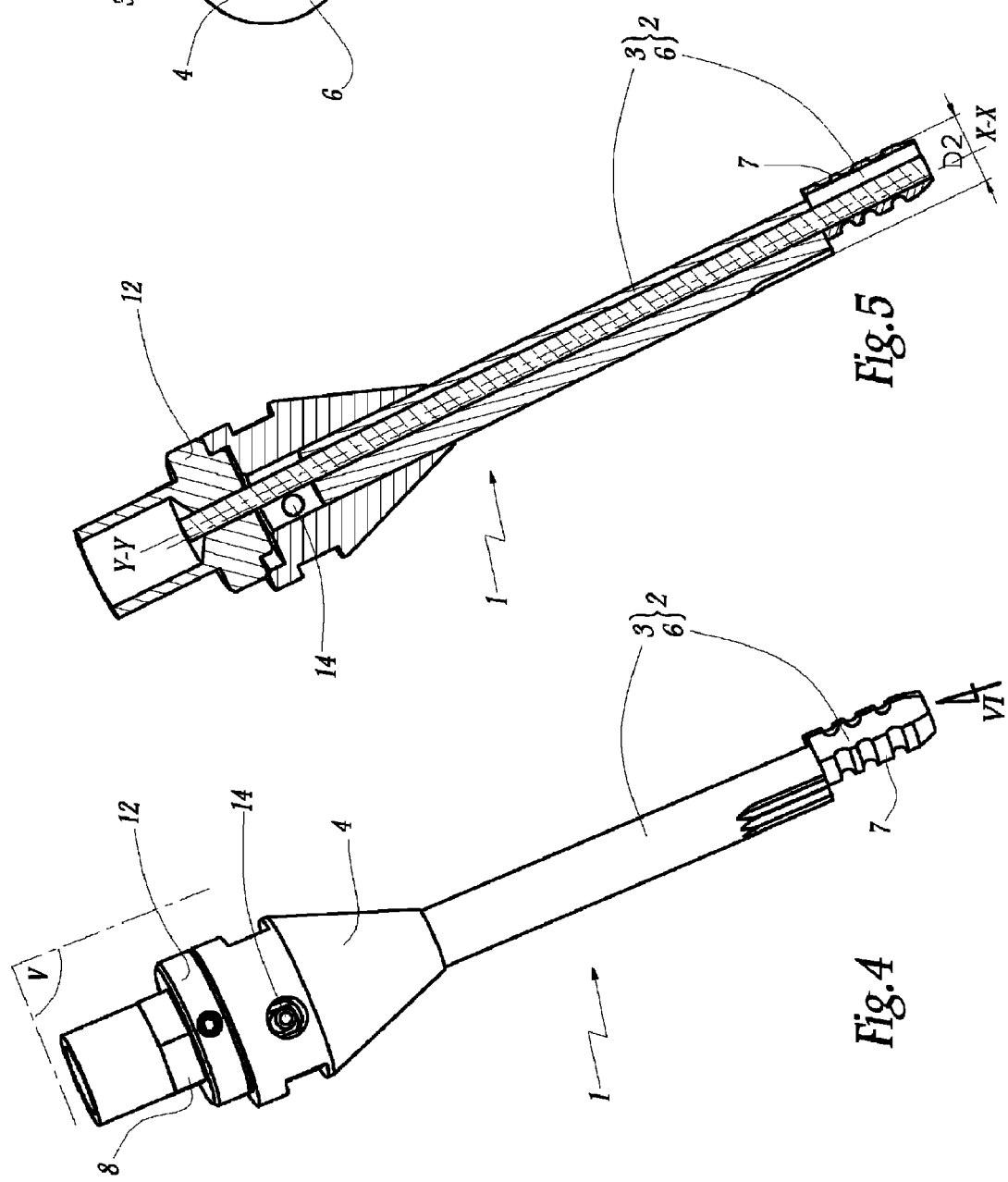

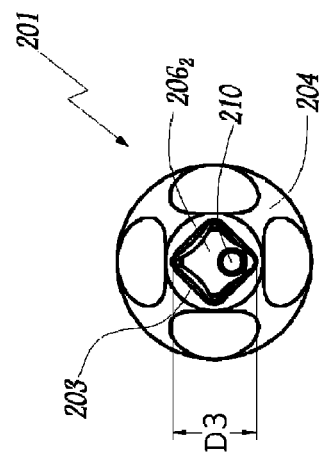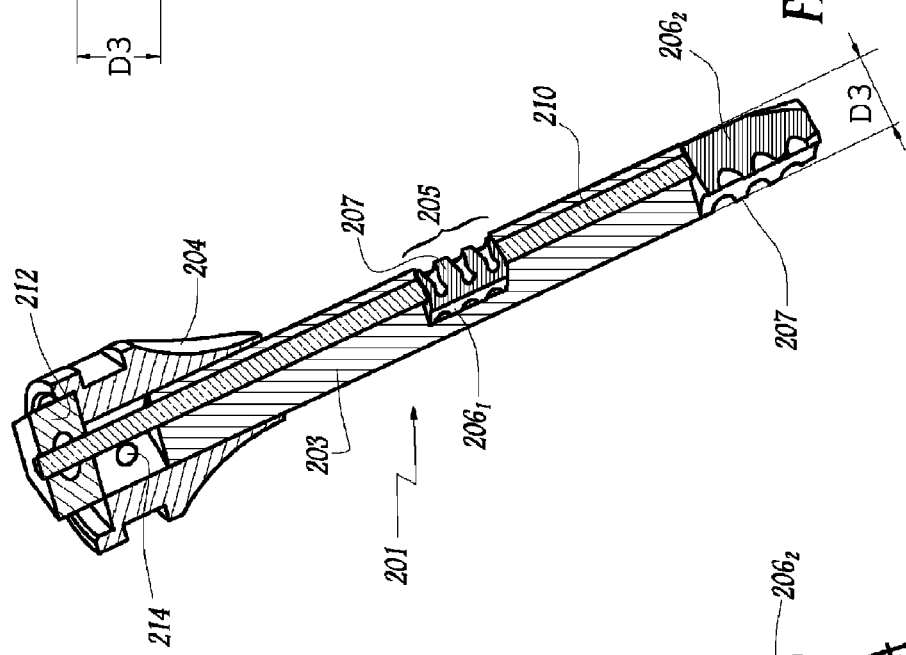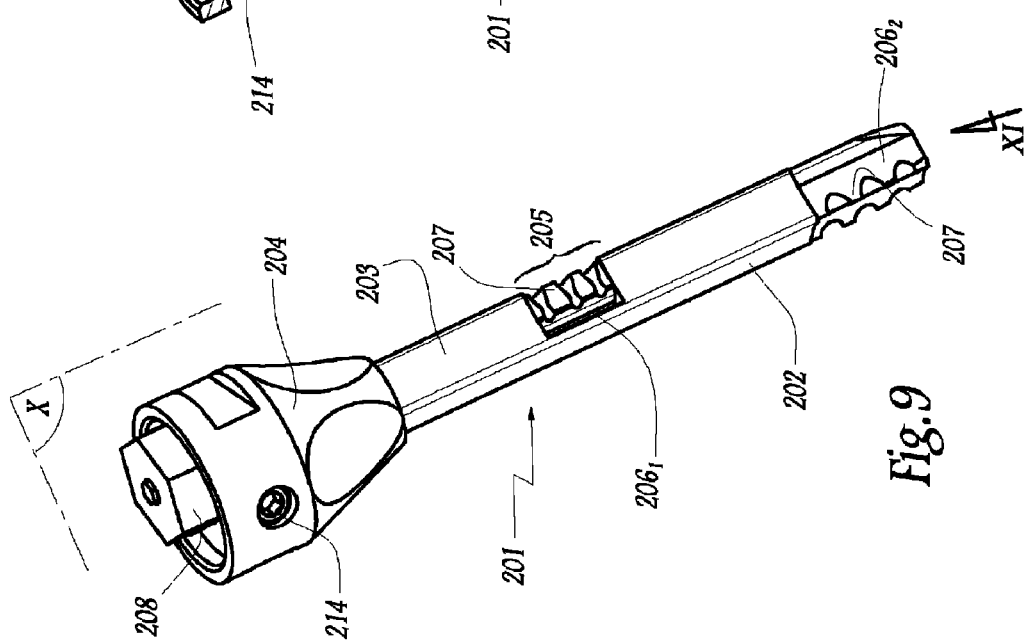

IMPLANT LOCKING DEVICE AND CORRESPONDING IMPLANT

TECHNICAL FIELD

The present invention relates to a device for trial or definitive locking of an implant and an implant comprising such a device.

BACKGROUND

Following a trauma to a shoulder or a hip, such as a fracture, implantation technology may be used. In this event, the implant is inserted into a corresponding long bone, namely the humerus or the femur. This application into such bones may be carried out provisionally or definitively.

Two types of implant are currently used. The first kind relates to a definitive or trial prosthesis which makes it possible to restore the articulation. The second type of implant corresponds to an osteosynthesis device, such as a nail. The nail, an implant temporary in nature, is used especially when it is wished to maintain pieces of the fractured bone in the original anatomical position and thus to induce a bone fusion.

In the case of applying a shoulder or hip prosthesis, the surgeon must ensure anatomic and durable reconstruction, as well as correct reconstruction of the biomechanical articulation properties.

Following a fracture of a humerus or a femur, it is known to reassemble the various bone fragments by means of a humeral or femoral nail respectively. In this case, the surgeon must ensure proper consolidation of the various pieces of the fractured bone.

Conventionally, the surgeon uses, for the two types of implants, locking devices described as external. For trial or definitive prostheses a positioning ancillary is commonly used. This tool makes it possible to stabilize the prosthesis once this has been inserted into the bone. In the case of a nail, it is in particular known to use screws for joining the lower end of the nail with the lower part of the diaphysis of the bone.

However, the use of such a tool or of such screws does not make the fixing of the prosthesis or of the nail easy for the surgeon. This is because the surgeon must provide an additional operating step. The operating time will therefore naturally increase. In addition to the complexity of fitting this tool or these screws, a change in the position of the prosthesis or of the screws may appear after the fitting of the implant. This may cause pain to the patient. A new operation may optionally be reprogrammed.

In order to eliminate this drawback, locking devices described as internal have been developed. Firstly, the surgeon inserts the prosthesis into the medullary canal of the bone. Subsequently, using a drive means, the humeral or femoral stem of the prosthesis increases its diameter homogeneously and symmetrically relative to its central axis until it is able to anchor itself in the bone.

However, such a locking device is not satisfactory as it does not enable effective locking of the prosthesis in the bone. This is because the rotational stability of this device is insufficient after its employment. The anchoring in the bone is for this reason less precise.

SUMMARY

The aim of the present invention is to provide a device for locking an implant enabling a saving in operating time for the surgeon when applying the implant, while ensuring that the implant is fastened to the bone in a satisfactory and precise manner.

To this end, the subject of the invention is a locking device for an implant in a long bone comprising:
  an elongate body designed to be received in a medullary canal of the long bone, the body defining, in a first position called the insertion position, a first transverse size and, in a second position called the locking position, a second transverse size greater than the first transverse size;
  drive means suited to enable the body to move from the first position to the second position;
  characterized in that the elongate body comprises:
  a central member defining a main axis;
  at least one locking member defining at least one axis of movement distinct from the main axis, the or each locking member being suited to anchoring itself in the long bone under the effect of the drive means.

Using the device according to the invention the simplification and the effectiveness of the joining of the implant in the bone makes it possible for the surgeon to reduce the operating time, while offering him the possibility of carrying out several repositionings of the implant. The risk of any operational complication is therefore limited directly.

According to further advantageous features of the implant locking device according to the invention, taken in isolation or in all technically possible combinations:
  one axis of movement is an axis of translation so that the or each locking member is suited to carry out a rotation around the axis of rotation under the effect of the drive means, such that at least one of the locking members projects laterally in relation to the central member;
  one axis of movement is an axis of translation so that the or each locking member is suited to carry out a translation relative to the central member under the effect of the drive means, such that at least one of the locking members projects laterally in relation to the central member;
  the ratio between the second transverse size and the first transverse size is greater than or equal to 1.15, and preferably greater than or equal to 1.5;
  at least one locking member is provided with roughness intended to be anchored in the walls of the medullary canal of the long bone when the device is in the second position;
  the drive means are suited to enable the elongate body also to move from the second position to the first position;
  the drive means comprise a rod suitable for driving the or each locking member and rotation means for rotating the rod;
  the device furthermore comprises locking means intended to lock the device once the elongate body is in the second position;
  the locking means comprise a screw, suitable for locking the rod;
  the elongate body comprises a first locking member, suitable for being housed in an opening of the elongate body in the first position, and a second locking member, suitable for being located in line with the central member;
  the central member and at least one of the locking members are approximately tubular.

The invention also relates to an implant comprising a locking device as defined above.

According to other advantageous features of the implant according to the invention, taken in isolation or in all technically possible combinations:
  the implant is a definitive shoulder, hip, or tibia prosthesis;

the implant is a trial shoulder, hip, or tibia prosthesis;

the implant is a humeral, femoral or tibial nail.

The subject matter of the invention is also a method for locking an implant in a long bone comprising the following steps:

a) insertion of an implant into a long bone comprising a locking device equipped with:

an elongate body designed to be received in a medullary canal of the long bone, the body defining, in a first position called the insertion position, a first transverse size and, in a second position called the locking position, a second transverse size greater than the first transverse size;

drive means suited to enable the body to move from the first position to the second position;

the elongate body comprising:

a central member defining a main axis;

at least one locking member defining at least one axis of movement distinct from the main axis, the or each locking member being suited to anchoring itself in the long bone under the effect of the drive means, b) actuation of the drive means, which causes a displacement of at least one of the locking members so that the implant anchors itself in the medullary canal of the bone.

BRIEF DESCRIPTION OF THE DRAWINGS

The invention will be better understood on reading the following description, provided solely by way of nonlimiting examples and with reference to the drawings, in which:

FIG. 1 shows a perspective view of an implant locking device according to the present invention in a first position;

FIG. 2 is a sectional view through plane II in FIG. 1;

FIG. 3 is a view from below of the device, according to the arrow III in FIG. 1;

FIG. 4 is a perspective view of the device in a second position;

FIG. 5 is a sectional view through plane V in FIG. 4;

FIG. 6 is a view from below of the device, according to the arrow VI in FIG. 4;

FIG. 9 shows a perspective view of an implant locking device according to a second embodiment of the present invention in the first position;

FIG. 10 is a sectional view through plane X in FIG. 9;

FIG. 11 is a view from below of the device, according to the arrow XI in FIG. 9;

DETAILED DESCRIPTION

Figure 7:
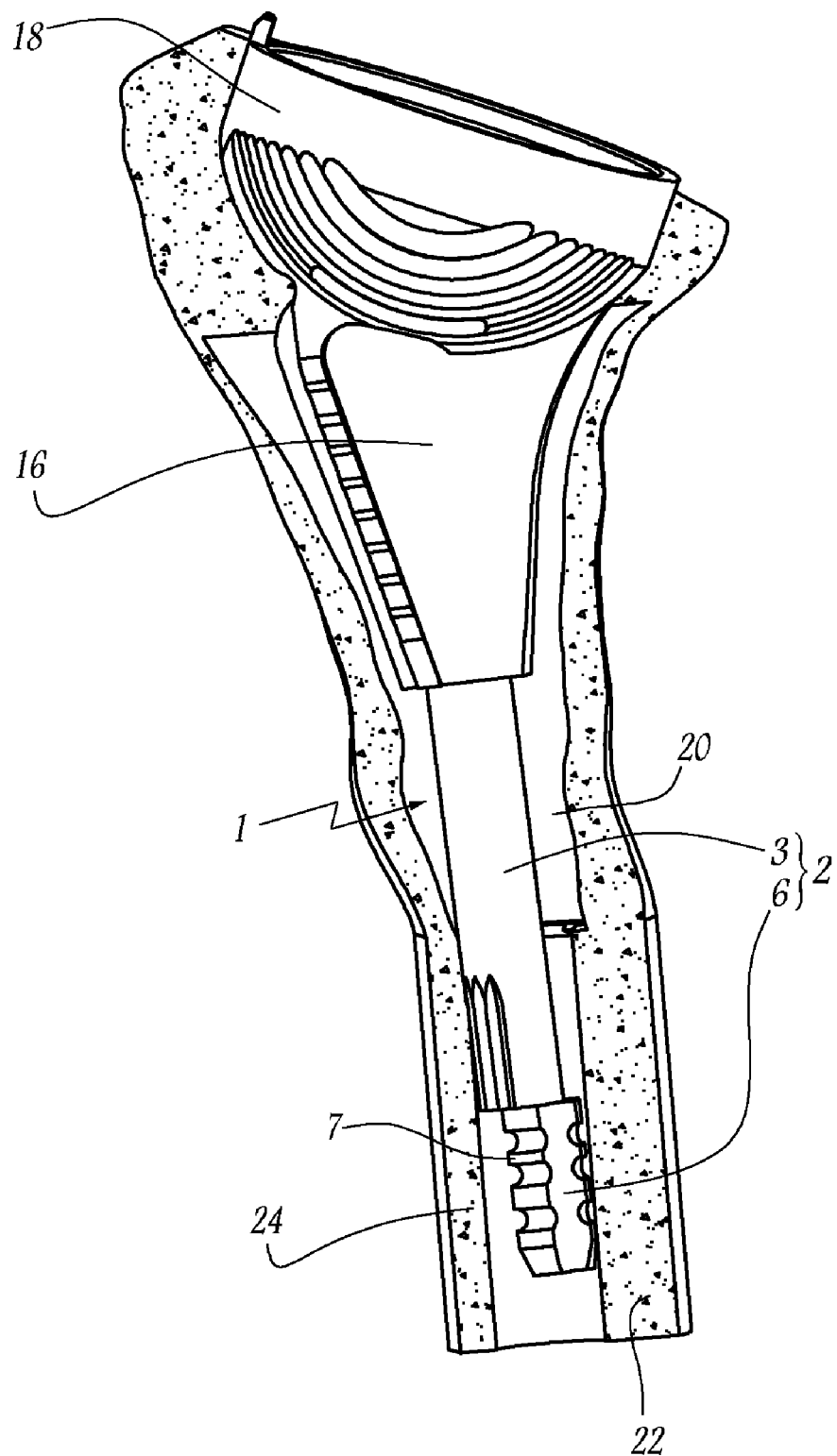
FIG. 7 is a perspective view of a trial prosthesis comprising a locking device according to the present invention.

FIG. 1 shows an implant locking device 1. The device 1 comprises a cylindrical elongate body 2. The body 2 comprises a cylindrical central member 3 with a main axis X-X, shown in FIG. 2, and an approximately tubular locking member 6. This locking member 6 is located in line with the central member 3, while being movable relative to this member 3. A tapered part 4 covers the upper part of the elongate body 2.

The device furthermore comprises drive means 8 making it possible to drive the locking member 6. In FIG. 2 the various elements of the drive means 8 are distinguished. These means 8 comprise a rod 10, the upper end of which is enclosed in a rotation means 12. The rod 10, tubular in form, defines an axis of rotation Y-Y substantially parallel to and offset in relation to the axis X-X. The rotation means 12 is a hollow and substantially cylindrical part suited to cooperate, by way of example, with a hexagonal tool or similar (not shown).

The locking member 6 is preferably provided with roughness 7 so that the anchoring in a bone takes place effectively. By way of nonlimiting example, it may be provided with a toothed profile. It is also conceivable for the central member 3 also to be provided with a toothed profile on its lower part close to the locking member 6. This profile is produced only over an area intended to come into contact with the bone. This facilitates the anchoring of the device 1 in the bone.

In FIGS. 2 and 3, the elongate body 2 defines a transverse size D1 corresponding to the diameter of the cylindrical elongate body 2. It should be noted that this size D1 is approximately the same both for the central member 3 and for the locking member 6, since the locking member 6 is in line with the central member 3.

Locking means 14 may also be provided whose function is in particular to prevent untimely movement of the rotation means 12. The locking means comprise a screw inserted in a threaded hole in the upper part of the tapered part 4. The screw can be moved between two positions. The first position, called the free position, is defined to be when the screw is at a distance from the rod 10. Conversely, the second position, called the lock position, is defined to be when the screw is in contact with the rod 10.

In a first neutral position called the insertion position, shown in FIGS. 1 to 3, the locking member 6 is located in line with the central member 3. As indicated in FIG. 3, the central member 3 is retracted relative to the locking member 6. This is because the central member 3 and the locking member 6 are defined by the same transverse size D1. The lock means 14 may be actuated and thus ensure the stability of the device 1 in the insertion position.

FIGS. 4 to 6 show the device 1 in a second position called the locking position. In order to move from the first position to the second position, the locking means 14 are released if they have been actuated. Then, by way of example, it is possible to turn the rotation means 12 by an angle of 180° relative to the axis Y-Y while locking the tapered part 4 by means of a suitable instrument.

The relative movement of the locking member 6 relative to the central member 3 is not limited to the two predefined positions respectively called the insertion and locking positions. The anchoring of the locking member 6 in a long bone may take place progressively.

As shown in FIGS. 5 and 6, at present the elongate body 2 defines a transverse size D2 which is greater than the transverse size D1. The rotation of the locking member 6 leads to its becoming eccentric relative to the central member 3. Specifically, the axis of rotation X-X is offset relative to the axis Y-Y. The locking member 6 therefore projects in a transverse manner, i.e. laterally, relative to the central member 3. The transverse size D2 may be defined as being the distance separating an edge of the central member 3 and an opposite edge of the locking member 6.

FIG. 7 shows a trial shoulder prosthesis 16 comprising the device 1 along with a metaphysis 18 screwed to the device 1. Other types of assembly are conceivable. It is also possible to make provision for the metaphysis 18 and the device 1 to be made of one piece. In a first period, the device 1 is in the first position, called the insertion position. The elongate body 2 is therefore defined by its transverse size D1. This size enables it to be inserted easily into a medullary canal 20 of a long bone 22.

In a second period, once the prosthesis 16 has been inserted into a diaphyseal part 24 of the bone 22, the rotation means 12 (not shown in FIG. 7) are actuated. To achieve this, it is possible, by way of example, to lock the metaphysis 18 using a suitable instrument. The locking member 6 rotates relative to the axis Y-Y so as progressively to increase the transverse size D2 of the elongate body 2. The locking member 6 therefore anchors itself in the bone 22. The prosthesis 16 thus finds itself in the second position, called the locking position. Optionally, it is also possible to screw the locking means 14 (not shown in FIG. 7) so as to lock the locking member 6 in the bone 22.

Once the trial prosthesis 16 is in the locking position, the surgeon locates the pieces of bone 22, then ensures that this application is stable. If this is not the case, he once again puts the prosthesis 16 into the first position called the insertion position. To do this, he actuates the rotation means 12 in the reverse direction to that of the first rotation, described above. He then removes the prosthesis 16 from the bone 22 then puts it in a new position.

When the positioning of the trial prosthesis 16 is correct, the surgeon notes the exact position then removes the prosthesis 16. He then applies the definitive prosthesis in the same position. This prosthesis may also be equipped with the device 1 or be fixed conventionally, i.e. with cement for example.

Figure 8:
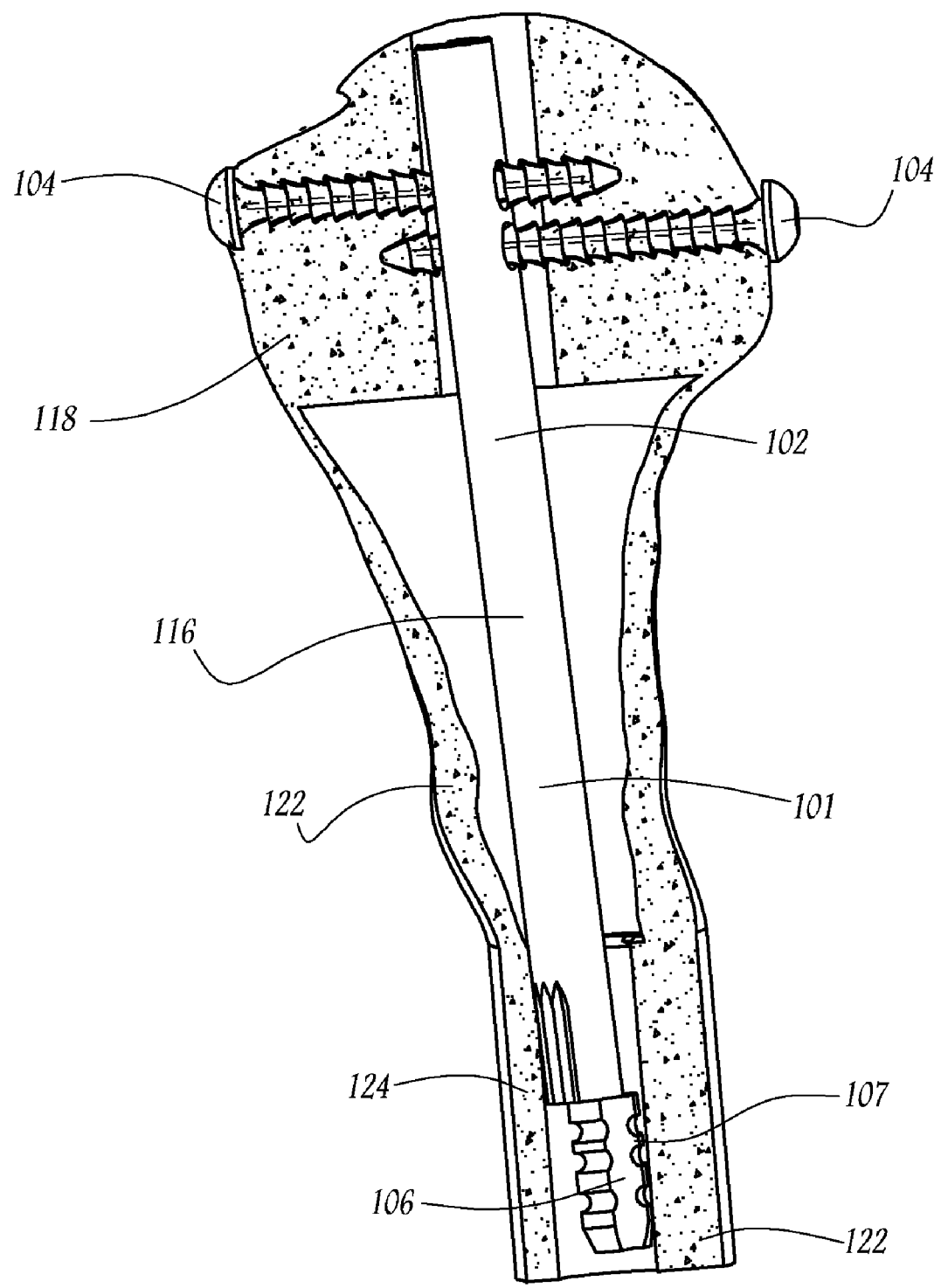
FIG. 8 is a perspective view of a nail comprising a locking device according to the present invention.

FIG. 8 shows a humeral nail 116 equipped with a locking device 101, similar to the device 1 presented in FIG. 7. In FIG. 8 the same elements are defined by the same reference numbers as in FIGS. 1 to 7 incremented by the number 100.

The device 101 is covered by a cap 102 which is suitable for allowing the insertion of the screw 104. The device 101 is, in a first period, in the first insertion position. The nail 116 is then inserted into the diaphyseal part 124 of the bone 122.

The locking member 106 is then rotated by actuating the rotation means (not shown). Once the locking member 106, provided with roughness 107, is well anchored in the diaphyseal part 124, fragments of bone are reassembled in order to restore the metaphysis 118 of the bone 122. These fragments are then joined by means of two screws 104.

In FIGS. 9 to 14 the same elements are defined by the same reference numbers as in FIGS. 1 to 6 incremented by the number 200.

FIG. 9 shows the implant locking device 201. The device 201 comprises the elongate body 202 of substantially tetragonal cross section. More generally, a polygonal cross section may be provided. This particular shape thus prevents, through friction relative to the walls of the medullary canal, rotational movement of the prosthesis. The body 202 comprises the central member 203 provided with an opening 205 and two locking members $206_1$, $206_2$. The first locking member $206_1$ is housed in the opening 205.

The device 201 furthermore comprises drive means 208 making it possible to drive both the first locking member $206_1$ and the second locking member $206_2$. The drive means 208 comprise the rod 210 joined to the rotation means 212.

The two locking members $206_1$, $206_2$ are provided with roughness 207. The presence of two locking members $206_1$, $206_2$ makes the anchoring of the device 201 in a long bone correspondingly more satisfactory. They thus prevent vertical movement of the device 201.

In FIGS. 10 and 11, the elongate body 202 defines a transverse size D3 corresponding approximately to the diametral size of the elongate body 202.

It is also possible to foresee the presence of locking means 214 so as to prevent movement of the rotation means 212.

In the first insertion position, shown in FIGS. 9 to 11, the first locking member $206_1$ is housed entirely in the opening 205 and the second locking member $206_2$ in turn is in line with the central member 203. The central member 203 and the two locking members $206_1$, $206_2$ define a first transverse size D3, shown in FIGS. 10 and 11.

Figure 14:
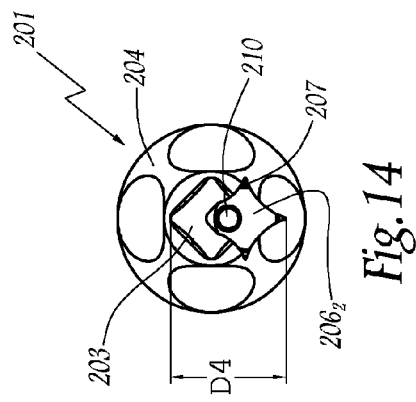
FIG. 14 is a view from below of the device, according to the arrow XIV in FIG. 12.
Figure 13:
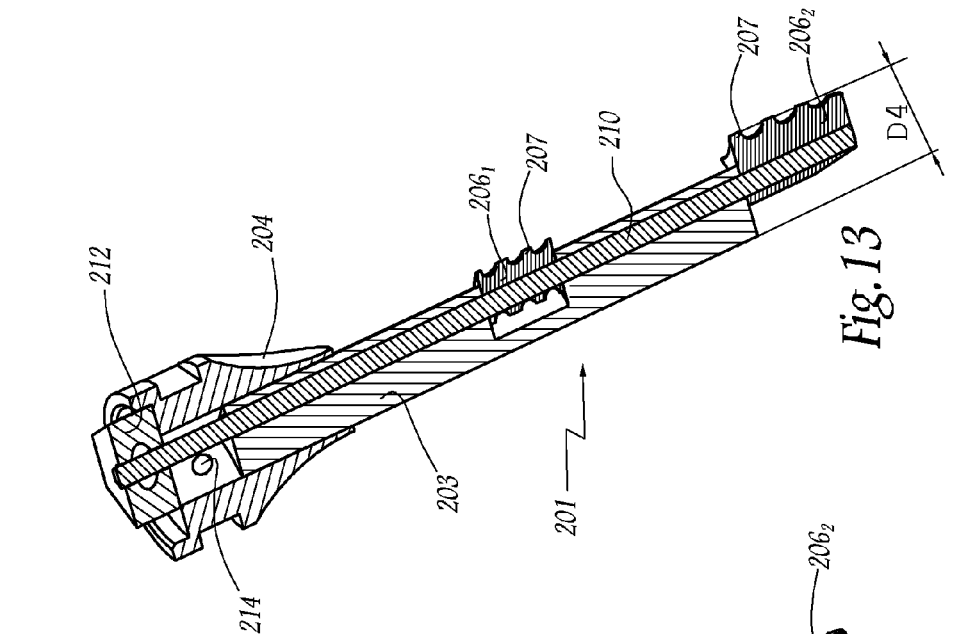
FIG. 13 is a sectional view through plane XIII in FIG. 12.
Figure 12:
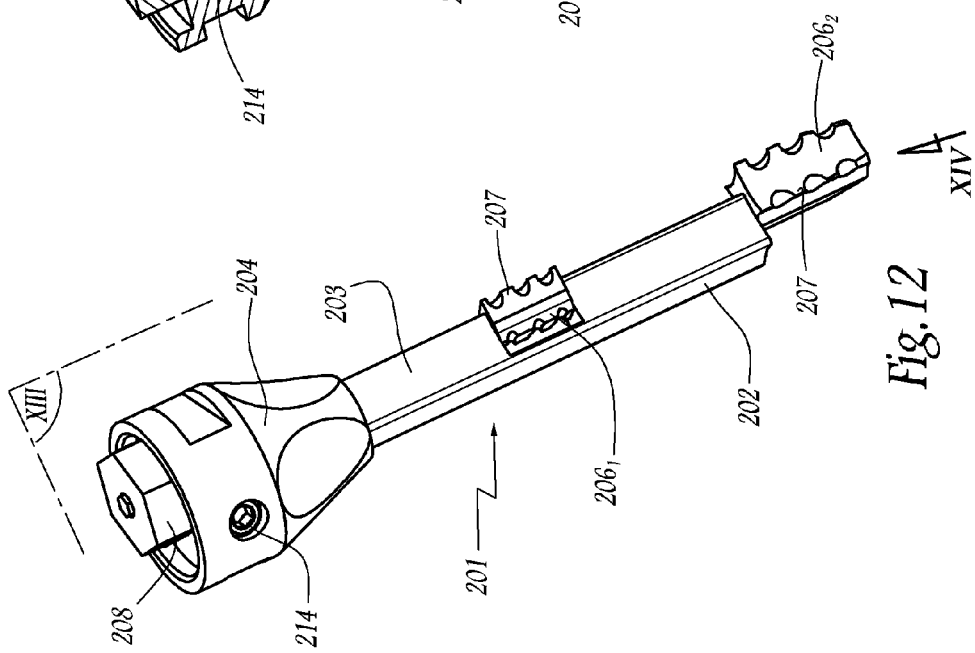
FIG. 12 is a perspective view of the device according to the second embodiment in the second position.

FIGS. 12 to 14 show the device 201 in a second position called the locking position.

As shown in FIGS. 13 and 14, at present the elongate body 202 defines a second transverse size D4 which is greater than the first transverse size D3. As previously explained in the context of the description of FIGS. 1 to 6, this is due to the fact that the main axis of the central member 203 is offset relative to the axis of rotation of the two locking members $206_1$, $206_2$. After rotating the two locking members $206_1$, $206_2$, these two members project in a transverse manner relative to the central member 203.

Similarly, it is possible to imagine the presence of several openings in the central member 203. Several locking members can then be accommodated in these openings.

Advantageously, the ratio between the second transverse size D2 or D4 defined by the locking position and the first transverse size D1 or D3 defined by the insertion position is greater than or equal to 1.15, and preferably it is greater than or equal to 1.5. Thus it is ensured that the prosthesis 16 and the nail 116, respectively equipped with the device 1, 101, 201, become wedged in the bone 22, 122 quickly and effectively.

By way of a variant (not shown), the invention may equally be applied to a definitive or trial hip prosthesis, and to a femoral nail. In other words, the use of the device 1, 101, 201 is not limited to a shoulder prosthesis or to a humeral nail, as shown in FIGS. 7 and 8.

Moreover, other types of relative movement between the central member and at least one locking member can be envisaged. Specifically, the axis of rotation (Y-Y) may, more generally, be an axis of movement, and in particular a translation axis, such that the or each locking member (6, 106, $206_1$, $206_2$) carries out a translation relative to the central member (3, 203) under the effect of drive means (8, 208), so that at least one of the locking members projects relative to the central member. The locking member can then anchor itself in the long bone (22, 122).

A combination of a rotation and a translation between the central member and at least one of the locking members is also conceivable.

Diverse arrangements and variants of the implant insertion and locking device described above are moreover conceivable. By way of example:
  other locking means 14 are conceivable; by way of example, a thrust ball bearing may be used;
  the part 4 is not necessarily tapered in shape; it is possible, for example, to envisage it in cylindrical shape;
  the substantially tubular elongate body 2 is not necessarily cylindrical or polygonal in shape; it is possible, for example, to foresee it in an oval shape; and/or
  the notion of a long bone is not limited to a femur or to a humerus; a tibia in particular is included in the scope of the use of the device.

The invention claimed is:

1. A locking device for an implant in a long bone, the locking device comprising:
   an elongate body adapted to be received in a medullary canal of the long bone, the elongate body comprising:
      a central member having a main longitudinal axis;
      at least one locking member having at least one axis of rotation with respect to the central member, the at least one axis of rotation being distinct from the main longitudinal axis,
      wherein the elongate body has an insertion position in which the elongate body has a first transverse size and in which the at least one locking member is in line with the central member, and a locking position in which the elongate body has a second transverse size greater than the first transverse size;
   a drive mechanism configured to move the elongate body from the insertion position to the locking position to anchor the at least one locking member in the long bone.

2. The locking device of claim 1, wherein the at least one axis of movement is an axis of rotation, wherein the drive mechanism moves the elongate body from the insertion position to the locking position by rotating the at least one locking member about the axis of rotation, and wherein in the locking position at least one of the at least one locking member projects laterally with respect to the central member.

3. The locking device of claim 1, wherein the at least one axis of movement is an axis of translation, wherein the drive mechanism moves the elongate body from the insertion position to the locking position by translating the at least one locking member with respect to the central member, and wherein in the locking position at least one of the at least one locking member projects laterally with respect to the central member.

4. The locking device of claim 1, wherein a ratio of the second transverse size to the first transverse size is greater than or equal to 1.15.

5. The locking device of claim 4, wherein the ratio is greater than or equal to 1.5.

6. The locking device of claim 4, wherein the first transverse size is a first maximum transverse diameter, and wherein the second transverse size is a second maximum transverse diameter.

7. The locking device of claim 1, the at least one locking member comprising a roughened area adapted for anchoring in walls of the medullary canal of the long bone when the elongate body is in the locking position.

8. The locking device of claim 1, wherein the drive mechanism is further configured to move the elongate body from the locking position to the insertion position.

9. The locking device of claim 2, wherein the drive mechanism comprises:
   a rod configured to rotate the at least one locking member; and
   a rotation mechanism configured to rotate the rod.

10. The locking device of claim 1, further comprising a locking member configured to lock the elongate body in the locking position.

11. The locking device of claim 9, further comprising a locking member configured to lock the elongate body in the locking position, wherein the rod comprises an aperture, the locking member comprising a screw configured to be received in the aperture to prevent rotation of the rod with respect to the elongate body.

12. The locking device of claim 1, wherein the at least one locking member comprises a first locking member housed in a lateral opening of the elongate body in the insertion position, and a second locking member located in line with the central member.

13. The locking device of claim 1, wherein the central member and the at least one locking member are substantially tubular.

14. The locking device of claim 1, further comprising an implant.

15. The locking device of claim 14, wherein the implant is selected from the group consisting of: a shoulder prosthesis, a hip prosthesis, and a tibia prosthesis.

16. The locking device of claim 14, wherein the implant is a trial prosthesis selected from the group consisting of: a shoulder trial prosthesis, a hip trial prosthesis, and a tibia trial prosthesis.

17. The locking device of claim 14, wherein the implant is selected from the group consisting of: a humeral nail, a femoral nail, and a tibial nail.

18. The locking device of claim 1, wherein the at least one axis of rotation is substantially parallel to and offset from the main longitudinal axis.

19. A method for locking an implant in a long bone, the method comprising:
   inserting an implant into a medullary canal of the long bone, wherein the implant comprises a locking device, and wherein the locking device comprises:
      a central member having a main longitudinal axis;
      at least one locking member having at least one axis of movement distinct from the main longitudinal axis,
      wherein the elongate body has an insertion position in which the elongate body has a first transverse size and in which the at least one locking member is in line with the central member, and a locking position in which the elongate body has a second transverse size greater than the first transverse size; and
   rotating the at least one locking member with respect to the central member about the at least one axis of movement in order to move the elongate body from the insertion position to the locking position to anchor the implant into the medullary canal.

20. The locking device of claim 19, wherein the at least one axis of movement is an axis of rotation, and wherein moving the elongate body from the insertion position to the locking position comprises rotating the at least one locking member about the axis of rotation, such that at least one of the at least one locking member projects laterally with respect to the central member.

21. The locking device of claim 19, wherein the at least one axis of movement is an axis of translation, and wherein moving the elongate body from the insertion position to the locking position comprises translating the at least one locking member with respect to the central member, such that at least one of the at least one locking member projects laterally with respect to the central member.

22. A locking device for an implant in a long bone, the locking device comprising:
   an elongate body adapted to be received in a medullary canal of the long bone, the elongate body comprising:
      a central member having a main longitudinal axis;
      at least one locking member having at least one axis of movement distinct from the main longitudinal axis and substantially parallel to the main longitudinal axis, wherein the elongate body has an insertion position in which the elongate body has a first transverse size and in which the at least one locking member is in line with the central member, and a locking position in which the elongate body has a second transverse size greater than the first transverse size;

a drive mechanism configured to move the elongate body from the insertion position to the locking position to anchor the at least one locking member in the long bone.

* * * * *